United States Patent
Greene, Jr. et al.

[11] Patent Number: 5,534,011
[45] Date of Patent: Jul. 9, 1996

[54] METHOD AND APPARATUS FOR THREADING A SUTURE ANCHOR

[75] Inventors: George R. Greene, Jr., Costa Mesa; Rodney Brenneman, Laguna Beach, both of Calif.

[73] Assignee: Vesica Medical, Inc., San Clemente, Calif.

[21] Appl. No.: 330,343

[22] Filed: Oct. 27, 1994

[51] Int. Cl.⁶ .................................................. A61B 17/04
[52] U.S. Cl. ............................................ 606/232; 606/73
[58] Field of Search ................................ 606/72, 73, 74, 606/75, 232, 148, 187, 139

[56] References Cited

U.S. PATENT DOCUMENTS

| | | | |
|---|---|---|---|
| 424,518 | 4/1890 | Van Norman . | |
| 2,042,403 | 5/1936 | Hrivnak | 223/99 |
| 3,877,434 | 4/1975 | Ferguson et al. | 128/327 |
| 4,265,246 | 5/1981 | Barry | 606/187 |
| 4,392,495 | 7/1983 | Bayers | 606/224 |
| 4,632,100 | 12/1986 | Somers et al. | 128/92 |
| 4,641,652 | 2/1987 | Hutterer et al. | 128/334 |
| 4,738,255 | 4/1988 | Goble et al. | 128/92 |
| 4,779,616 | 10/1988 | Johnson | 128/334 |
| 4,803,984 | 2/1989 | Narayanan et al. | 128/334 |
| 4,899,743 | 2/1990 | Nicholson et al. | 606/139 |
| 4,946,468 | 8/1990 | Li | 606/232 |
| 4,968,315 | 11/1990 | Gatturna | 606/72 |
| 5,022,550 | 3/1991 | Li | 606/139 |
| 5,078,721 | 1/1992 | McKeating | 606/139 |
| 5,078,730 | 1/1992 | Li et al. | 606/228 |
| 5,152,790 | 10/1992 | Rosenberg et al. | 623/13 |
| 5,156,616 | 10/1992 | Meadows et al. | 606/232 |
| 5,207,679 | 5/1993 | Li | 606/72 |
| 5,217,486 | 6/1993 | Rice et al. | 606/232 |
| 5,250,054 | 10/1993 | Li | 606/148 |
| 5,336,231 | 8/1994 | Adair | 606/148 |
| 5,370,662 | 12/1994 | Stone et al. | 606/73 |

OTHER PUBLICATIONS

"GII Anchor System" Brochure published by Miteck Products, Inc. 1994.

*Primary Examiner*—Gary Jackson
*Assistant Examiner*—Sonya Harris-Ogugua
*Attorney, Agent, or Firm*—Klein & Szekeres

[57] ABSTRACT

A method for threading a suture through a suture anchor after the anchor has been driven into a bone comprises the steps of (1) providing a suture anchor having an eyelet, with at least a portion of a pre-installed suture engaging implement passed through the eyelet; (2) driving the suture anchor into a bone, leaving the eyelet and the suture engaging implement exposed; (3) engaging a suture with the suture engaging implement; (4) removing the suture engaging implement from the eyelet so as to pull the suture through the eyelet; and (5) disengaging the suture engaging implement from the suture. In one embodiment, the suture engaging implement comprises a thin, flexible tube having an open end. The tube is pre-installed in the anchor by passing it through the eyelet. One end of the suture is pushed into the open end of the tube. The tube is pulled out of the eyelet so as to pull the suture through the eyelet. The end of the suture is then removed from the open end of the tube. A second embodiment employs a loop of flexible, filamentous material as the suture engaging implement. The loop is pre-installed in the anchor by passing a portion of the loop through the eyelet. One end of the suture is passed through the portion of the loop that has been passed through the eyelet. The loop is pulled out of the eyelet so as to pull the suture through the eyelet. The suture is then removed from the loop.

12 Claims, 2 Drawing Sheets

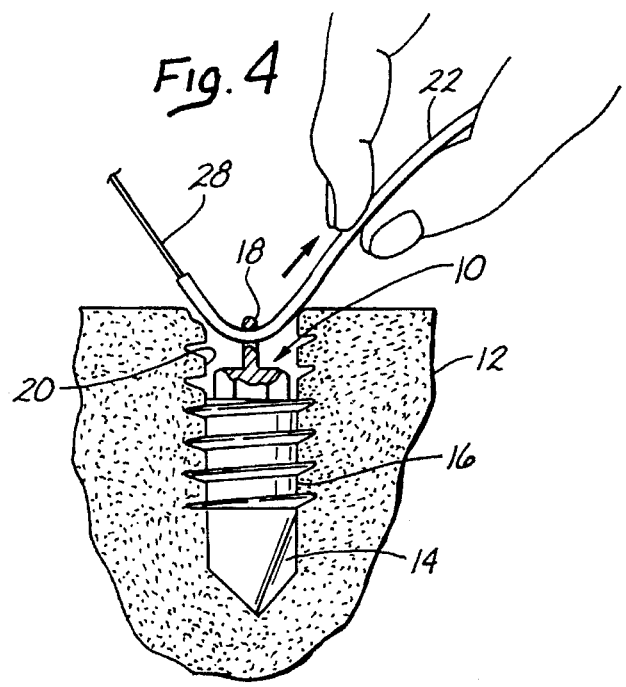
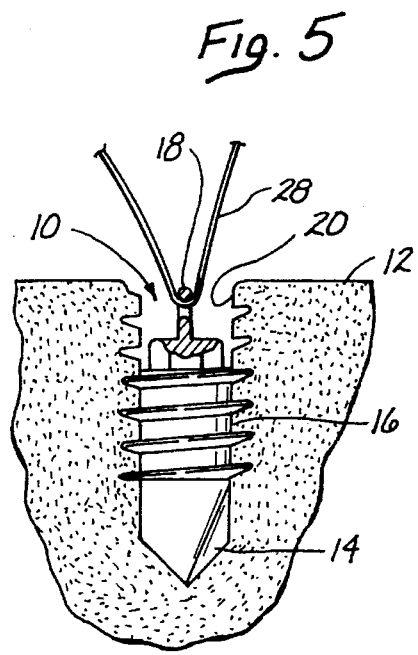
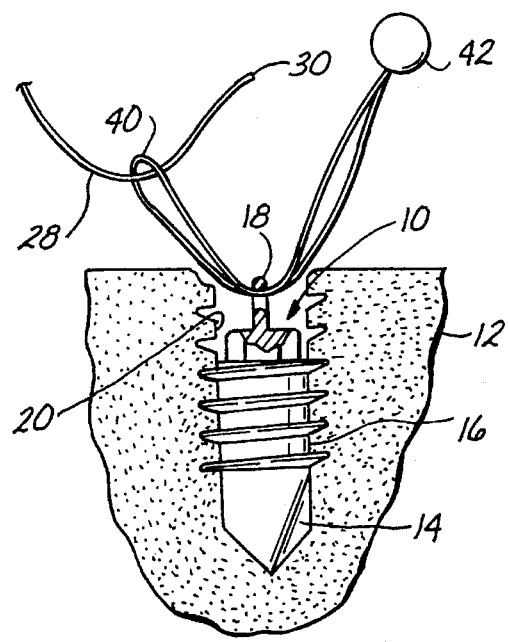
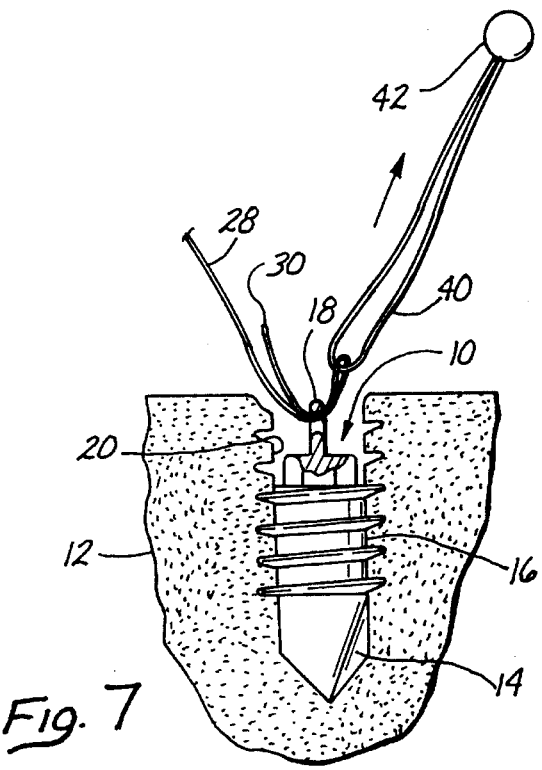

METHOD AND APPARATUS FOR THREADING A SUTURE ANCHOR

BACKGROUND OF THE INVENTION

This invention relates generally to the field of surgical methods and apparatus for anchoring a suture to a bone mass, so that the suture can be used to secure a ligament or other tissue to the bone mass.

More specifically, the present invention relates to a method and apparatus for threading a suture through a suture anchor after the suture anchor has been driven into a bone mass.

In numerous surgical procedures, an object is either directly attached to a bone, or is indirectly attached to the bone with a suture. In the former case, a ligament or a prosthesis may be directly attached to the bone. In the latter case, bodily tissue may be supported by sutures that are anchored in the bone, thereby using the bone as a structural support. An example of this latter type of procedure is the percutaneous bladder neck suspension, in which sutures anchored in the pelvis are attached to tissue adjacent to the urethra to support and thereby suspend the bladder neck.

Various types of suture anchors have been devised to anchor the suture to the bone, as exemplified by the following U.S. patents: U.S. Pat. No. 4,632,100—Somers et al.; U.S. Pat. No. 4,899,743—Nicholson et al.; U.S. Pat. No. 4,946,468—Li; U.S. Pat. No. 4,968,315—Gatturna; U.S. Pat. No. 5,002,550—Li; U.S. Pat. No. 5,156,616—Meadows et al.; U.S. Pat. No. 5,207,679—Li; and U.S. Pat. No. 5,217,486—Rice et al.

The prior art suture anchors, exemplified by the above-noted patents, require the suture to be threaded through the anchor before the anchor is installed in the bone mass. In some cases, however, installing an anchor that is pre-threaded with a suture may present some problems. For example, in using suture anchors of the self-tapping, threaded shank type (see, e.g., U.S. Pat. No. 4,632,100—Somers at al. and U.S. Pat. No. 5,156,616—Meadows et al., supra) that require a twisting motion for installation, the suture may be prone to being twisted during installation. This is especially a problem when it is necessary to thread a suture through two anchors, since, with both anchors pre-threaded with the suture, twisting of the suture during installation of the second anchor is virtually inevitable. Furthermore, care must be taken, during installation of a self-tapping anchor that is pre-threaded with a suture, to avoid abrasion of the suture by the anchor driving tool.

Thus, there are often times when it would be advantageous, or even necessary, to thread the suture through the suture anchor after the anchor has been installed. This, however, may be difficult to do in practice, due to the thinness and limpness of the suture, the small size of the anchor eyelet through which the suture must be threaded, and the confined space at the surgical site for manipulation of the suture (especially in percutaneous procedures).

Accordingly, there has been a long felt need for a method and associated apparatus for threading a suture through a suture anchor in situ after the anchor has been installed. It would be of additional advantage if such a method and apparatus would be economical to manufacture and simple to use.

SUMMARY OF THE INVENTION

Broadly, the present invention is a method of threading a suture through the exposed eyelet of a suture anchor after the anchor has been installed, comprising the steps of: (1) providing a suture anchor having an eyelet, with at least a portion of a pre-installed suture engaging implement passed through the eyelet; (2) driving the suture anchor into a bone mass so as to leave the eyelet and the suture engaging implement exposed; (3) engaging a suture with the suture engaging implement; (4) removing the suture engaging implement from the eyelet so as to pull one end of the suture and a following portion of the length of the suture through the eyelet; and (5) disengaging the suture engaging implement from the suture.

In a first preferred embodiment, the suture engaging implement comprises a thin, flexible tube of biocompatible elastomeric material, having an open end, preferably slightly flared. The tube is pre-installed in the anchor by passing it through the eyelet as part of the first (providing) step of the above described method, and is thus in its proper position after the second (driving) step. The third (engaging) step comprises pushing one end of the suture into the open end of the tube. The fourth (removing) step comprises pulling the tube out of the eyelet so as to pull the one end of the suture and a following length of the suture through the eyelet. The fifth (disengaging) step comprises pulling the one end of the suture out of the open end of the tube.

A second preferred embodiment employs a loop of flexible, biocompatible wire as the suture engaging implement. The first step of the method comprises pre-installing the loop in the eyelet of the anchor by passing at least a portion of the loop through the eyelet; the second step comprises driving the anchor in a bone mass with the loop pre-installed in the eyelet; the third step comprises passing one end of the suture through the portion of the loop that has been passed through the eyelet; the fourth step comprises pulling the loop out of the eyelet so as to pull the one end of the suture and a following length of the suture through the eyelet; and the fifth step comprises removing the suture from the loop.

In both embodiments of the invention, the suture engaging implement is passed through the eyelet of the anchor before the anchor is driven into the bone mass. As a result, the risk of damage to the suture during installation of the anchor is eliminated, since the suture is threaded through the eyelet only after the anchor is installed. Furthermore, the use of the pre-installed suture engaging implement greatly facilitates the threading of the suture through the eyelet, which would otherwise be very difficult once the anchor is installed.

Thus, the present invention greatly facilitates post-installation threading of the suture anchor, thereby minimizing the above-described problems associated with the installation of anchors after they have been threaded with the suture. Moreover, in both embodiments of the invention, the suture engaging implement can be easily and inexpensively manufactured.

These and other advantages of the present invention will be more readily appreciated from the detailed description that follows.

BRIEF DESCRIPTION OF THE DRAWINGS

FIG. 4 is an elevational view, partially in cross section, showing the suture engaging implement of FIG. 1 being removed from the eyelet of the anchor so as to pull one end of the suture and a following length of the suture through the eyelet;

FIG. 5 is an elevational view, partially in cross section, showing the suture threaded through the eyelet upon completion of the threading method, after either embodiment of the suture engaging implement has been disengaged from the suture;

FIG. 6 is an elevational view, partially in cross section, showing a self-tapping suture anchor installed in a bone mass, with a pre-installed suture engaging implement, in accordance with a second preferred embodiment of the present invention, passed through the eyelet of the anchor, and further showing the implement engaged with the suture; and FIG. 7 is an elevational view, partially in cross section, showing the suture engaging implement of FIG. 6 being removed from the eyelet of the anchor so as to pull one end of the suture and a following length of the suture through the eyelet.

DETAILED DESCRIPTION OF THE INVENTION

Figure 1:
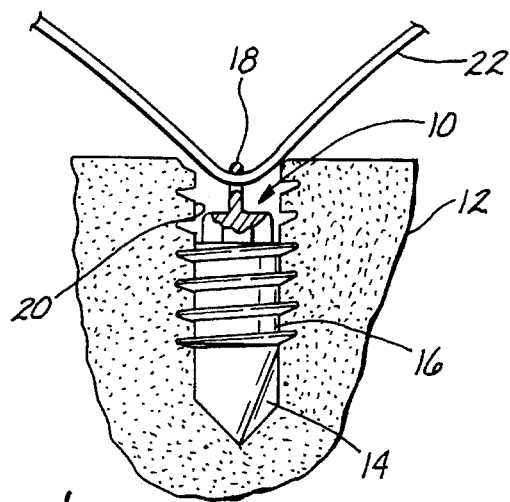
FIG. 1 is an elevation view, partially in cross section, showing a self-tapping suture anchor installed in a bone mass, with a pre-installed suture engaging implement, in accordance with a first preferred embodiment of the present invention, passed through the eyelet of the anchor.

Referring first to FIGS. 1 through 5, a first preferred embodiment of the invention is shown in conjunction with a self-tapping suture anchor 10, installed in a bone mass 12. The suture anchor 10 may be of the type disclosed in U.S. Pat. No. 4,632,100—Somers et al., for example, with a drilling portion 14 at its distal end, a threaded shank portion 16, and an eyelet 18 at its proximal end. While, in practice, the present invention is most advantageously used in conjunction with a screw-in or self-tapping suture anchor, other types of suture anchors (e.g., those which may be pushed or pressed into the bone) may be used, provided that they have an eyelet at the proximal end. The suture anchor 10 will hereinafter be described as being "driven" into the bone mass 12, and it should be understood that this term will encompass any method of installation of the anchor.

When the anchor 10 is driven into the bone mass 12 as shown, it bores a hole 20 in the bone mass 12, and the eyelet 18 is exposed at the outer terminus of the hole 20.

Figure 2:
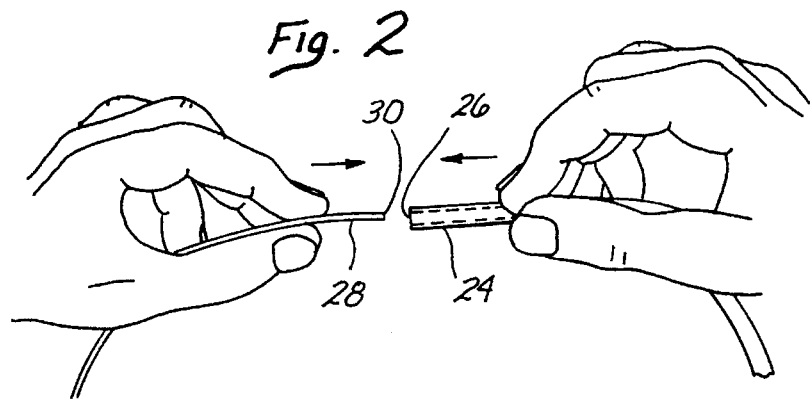
FIG. 2 is an elevational view showing the step of engaging a suture with the suture engaging implement of FIG. 1.

FIG. 1 illustrates the first and second steps in the method of the present invention: providing a suture anchor 10 with a pre-installed suture engaging implement, at least a portion of which has been passed through the eyelet 18 of the anchor 10; and driving the suture anchor 10 into the bone mass 12 with the pre-installed suture engaging implement, so as to leave the eyelet 18 and the suture engaging implement exposed. In accordance with the first preferred embodiment of the invention, the suture engaging implement comprises an elongate, flexible tube 22 of an elastomeric material, such as polyurethane. The tube 22 is hollow, with open ends. As shown in FIG. 2, the tube has at least one end 24 that has a flared opening 26. The tube 22 is of sufficient length so that the third step of the method, described below, may be easily performed.

Figure 3:
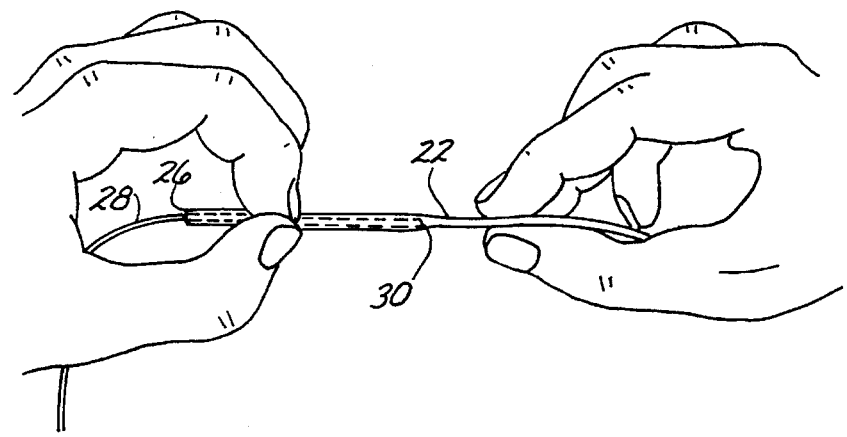
FIG. 3 is an elevational view, similar to that of FIG. 2, showing the suture fully engaged by the suture engaging implement of FIG. 1.

FIGS. 2 and 3 illustrate the third step in the method of the invention: engaging a suture 28 with the tube 22. In the first embodiment, this step is performed by pushing a first end 30 of the suture 28 into the flared opening 26 of the tube 22. The suture 28 is pushed into the tube 22 as far as it will easily travel, but at least about 9 to 10 mm. The inside diameter of the tube 22 is selected with respect to the outside diameter of the suture 28 so that the tube 22 allows passage of the suture 28 when the tube 22 is relaxed, but frictionally grips the suture 28 when the inside diameter of the tube 22 contracts as the tube is elastomerically stretched during the following (removing) step.

FIG. 4 illustrates the fourth step in the method of the invention: removing the suture engaging implement (the tube 22) from the eyelet 18 so as to pull the first end 30 of the suture 28 through the eyelet 18, along with a following portion of the suture 28 of the desired length. As mentioned above, the removal of the tube 22 by pulling it out of the eyelet 18 results in an elastomeric contraction of its inside diameter, thereby enhancing the grip of the tube 22 on the suture 28, and thus minimizing the likelihood that suture 28 will slip out of the tube 22. After the tube 22 is removed from the eyelet 18, it is further pulled away from the eyelet 18, until the desired length of the suture 18 has been threaded through the eyelet 18, after which the final step in the method is performed: disengaging the suture engaging implement (the tube 22) from the suture 28. This final step is performed by simply pulling the first end 30 of the suture 28 out of the tube 22, after which the threading of the suture 28 through the eyelet 18 is completed, as shown in FIG. 5.

FIGS. 6 and 7 illustrate a second preferred embodiment of the invention, in which the suture engaging implement comprises a loop 40, formed of a flexible, biocompatible, filamentous material, preferably a metal wire, such as stainless steel, although a wide range of substantially equivalent materials, both metallic and non-metallic, may also be used. The loop 40 may be formed by attaching the ends of a suitable length of wire to a metal knob or gripping member 42. The attachment may be by any suitable method, such as welding, soldering, or brazing, depending upon the materials used, keeping in mind that all materials must be biocompatible. Alternatively, the gripping member 42 may be a plastic element molded onto a continuous wire loop 40. The knob or gripping member 42 is shown as spherical; however, any suitable shape will serve as well.

FIG. 6 shows the first, second, and third steps in the method of the invention. The suture engaging implement (the loop 40) has been pre-installed into the eyelet 18 (first step), so that at least a substantial portion of it has been passed through the eyelet 18. The suture anchor 10 has been driven into the bone mass 12, along with the pre-installed loop 40 (second step), so as to leave the eyelet 18 and the loop 40 exposed. The suture 28 has been engaged with the loop 40 (third step) by passing the first end 30 of the suture 28 through the portion of the loop 40 that has been passed through the eyelet 18.

FIG. 7 shows the fourth step of the method of the invention: removing the suture engaging implement (the loop 40) from the eyelet 18 so as to pull the first end 30 of the suture 28 through the eyelet 18, along with a following portion of the suture 28 of the desired length. Finally, the loop 40 is disengaged from the suture 28 by removing the suture 28 from the loop 40, leaving the suture 28 threaded through the eyelet 18, as shown in FIG. 5.

As will be appreciated from the foregoing description, the present invention provides for the quick and easy threading of a suture through a suture anchor after the anchor has been installed. This is accomplished with apparatus (the suture engaging tube 22 and loop 40) that is sufficiently inexpensive to manufacture to be disposable.

Although two preferred embodiments have been described herein, it will be appreciated that a number of variations and modifications (some which have been alluded to above) may suggest themselves to those skilled in the pertinent arts. These variations and modifications should be considered within the spirit and scope of the present invention, as defined in the claims that follow.

What is claimed is:

1. A method for threading a suture having a first end and a following portion through an eyelet of a suture anchor, comprising the steps of:

(a) providing a suture anchor having an eyelet, with at least a portion of a pre-installed suture engaging implement installed in the eyelet;

(b) driving the suture anchor into a bone mass so as to leave the eyelet and the suture engaging implement exposed;

(c) engaging the suture engaging implement with a suture;

(d) removing the suture engaging implement from the eyelet so as to pull the first end of the suture and the following portion through the eyelet; and (e) disengaging the suture engaging implement from the suture.

2. The method of claim 1, wherein the suture engaging implement comprises an elongate, flexible, elastomeric hollow tube having an open end dimensioned to receive the suture, and wherein the step of engaging comprises:

pushing the first end of the suture into the open end of the tube.

3. The method of claim 2, wherein the open end of the tube includes a flared opening, and wherein the pushing step comprises:

pushing the first end of the suture into the flared opening.

4. The method of claim 2, wherein the step of removing comprises the step of:

stretching the tube so as to elastomerically contract its inside diameter, thereby frictionally gripping the suture.

5. A method for threading a suture having a first end and a following portion through an eyelet of a suture anchor, comprising the steps of:

(a) providing a suture anchor with an eyelet and an elongate, flexible, elastomeric, hollow tube having an open end, at least a portion of the tube having been installed in the eyelet;

(b) driving the suture anchor into a bone mass so as to leave the eyelet and the tube exposed;

(c) pushing the first end of the suture into the open end of the tube;

(d) removing the tube from the eyelet so as to pull the first end of the suture and the following portion of the suture through the eyelet; and (e) removing the suture from the tube.

6. The method of claim 5, wherein the open end of the tube includes a flared opening, and wherein the step of pushing comprises:

pushing the first end of the suture into the flared opening.

7. The method of claim 5, wherein the step of pushing comprises:

pushing the first end of the suture and at least about 9 to 10 mm in length of the following portion, into the open end of the tube.

8. The method of claim 7, wherein the step of removing comprises:

pulling the first end of the suture out of the open end of the tube.

9. The method of claim 5, wherein the step of removing the tube comprises the step of:

stretching the tube so as to elastomerically contract its inside diameter, thereby frictionally gripping the suture.

10. A method for threading a suture having a first end and a following portion through an eyelet of a suture anchor, comprising the steps of:

(a) providing a suture anchor having an eyelet and a flexible, filamentous loop, at least a portion of which has been installed in the eyelet;

(b) driving the suture anchor into a bone mass so as to leave the eyelet and the filamentous loop exposed;

(c) passing the first end of the suture through the portion of the loop that has been installed in the eyelet;

(d) removing the loop from the eyelet so as to pull the first end of the suture and the following portion of the suture through the eyelet; and (e) removing the suture from the loop.

11. The method of claim 10, wherein the loop comprises:

a length of flexible filamentous material having first and second ends; and a gripping member joined to the first and second ends of the length of filamentous material; and wherein the step of removing the loop comprises the steps of:

grasping the gripping member; and pulling the loop through the eyelet so as to pull the first end of the suture and the following portion thereof through the eyelet.

12. The method of claim 10, wherein the loop comprises:

a continuous metal wire loop; and a plastic gripping member molded onto the wire loop; and wherein the step of removing the loop comprises the steps of:

grasping the gripping member; and pulling the loop through the eyelet so as to pull the first end of the suture and the following portion thereof through the eyelet.

* * * * *